United States Patent
Barstow et al.

(10) Patent No.: US 11,053,493 B2
(45) Date of Patent: Jul. 6, 2021

(54) METHOD FOR ISOLATING DNA MOLECULES BY GENERATING A PROGENITOR COLLECTION CATALOG

(71) Applicant: The Trustees of Princeton University, Princeton, NJ (US)

(72) Inventors: Buz Barstow, Princeton, NJ (US); Michael Baym, Cambridge, MA (US); Lev Shaket, Palm Coast, FL (US); Isao Anzai, New York, NY (US); Oluwakemi Adesina, Lawrence, NJ (US)

(*) Notice: Subject to any disclaimer, the term of this patent is extended or adjusted under 35 U.S.C. 154(b) by 978 days.

(21) Appl. No.: 15/588,257

(22) Filed: May 5, 2017

(65) Prior Publication Data
US 2017/0321212 A1    Nov. 9, 2017

Related U.S. Application Data

(60) Provisional application No. 62/332,331, filed on May 5, 2016.

(51) Int. Cl.
| | |
|---|---|
| *C12N 15/10* | (2006.01) |
| *C12Q 1/6874* | (2018.01) |
| *G16B 30/00* | (2019.01) |
| *G16B 40/00* | (2019.01) |
| *G16B 20/50* | (2019.01) |

(52) U.S. Cl.
CPC ....... *C12N 15/1082* (2013.01); *C12N 15/102* (2013.01); *C12Q 1/6874* (2013.01); *G16B 20/50* (2019.02); *G16B 30/00* (2019.02); *G16B 40/00* (2019.02)

(58) Field of Classification Search
None
See application file for complete search history.

(56) References Cited

PUBLICATIONS

Anzai, Isao A., et al. "Rapid curation of gene disruption collections using Knockout Sudoku." nature protocols 12.10: 2110-2137. (Year: 2017).*
Anzai, Isao A., et al. "Knockout Sudoku, a method for rapidly curating gene disruption collections." PeerJ Preprints 4: e2294v1. (Year: 2016).*
Baym, Michael, et al. "Rapid construction of a whole-genome transposon insertion collection for Shewanella oneidensis by Knockout Sudoku." Nature communications 7.1: 1-13. (Year: 2016).*
Vandewalle, Kristof, et al. "Characterization of genome-wide ordered sequence-tagged Mycobacterium mutant libraries by Cartesian Pooling-Coordinate Sequencing." Nature communications 6.1: 1-7. (Year: 2015).*
DeJesus, Michael A., et al. "Bayesian analysis of gene essentiality based on sequencing of transposon insertion libraries." Bioinformatics 29.6: 695-703. (Year: 2013).*

* cited by examiner

*Primary Examiner* — G Steven Vanni
(74) *Attorney, Agent, or Firm* — Tarter Krinsky & Drogin LLP

(57) ABSTRACT

Systems and methods for isolating DNA molecules that can include the steps of: providing a transposon mutant collection, the transposon mutant collection being stored in a plurality of wells; dispatching aliquots from each well in the transposon mutant collection to a set of pools in a combinatorial pooling array that uses pool address coordinates, the aliquots being dispatched to the set of pools based on a location of the aliquots within the transposon mutant collection; constructing an amplicon library, the amplicon library including a sequencing dataset; parsing the sequencing dataset to a set of putative transposon insertion locations and pool address coordinates; calculating a likelihood for each location and pool address coordinates within the set of putative transposon insertion locations and pool address coordinates using a Bayesian inference algorithm informed by internal self-consistency; and generating a progenitor collection catalog based on location and pool address coordinates verified in the calculating step.

15 Claims, 9 Drawing Sheets

Specification includes a Sequence Listing.

|      | PC01 | PC02 | PC03 | PC04 | PC05 | PC06 | PC07 | PC08 | PC09 | PC10 | PC11 | PC12 | PC13 | PC14 | PC15 | PC16 | PC17 | PC18 | PC19 | PC20 | PC21 |
|------|------|------|------|------|------|------|------|------|------|------|------|------|------|------|------|------|------|------|------|------|------|
| PR01 | 1    | 2    | 3    | 4    | 5    | 6    | 7    | 8    | 9    | 10   | 11   | 12   | 13   | 14   | 15   | 16   | 17   | 18   | 19   | 20   | 21   |
| PR02 | 22   | 23   | 24   | 25   | 26   | 27   | 28   | 29   | 30   | 31   | 32   | 33   | 34   | 35   | 36   | 37   | 38   | 39   | 40   | 41   | 42   |
| PR03 | 43   | 44   | 45   | 46   | 47   | 48   | 49   | 50   | 51   | 52   | 53   | 54   | 55   | 56   | 57   | 58   | 59   | 60   | 61   | 62   | 63   |
| PR04 | 64   | 65   | 66   | 67   | 68   | 69   | 70   | 71   | 72   | 73   | 74   | 75   | 76   | 77   | 78   | 79   | 80   | 81   | 82   | 83   | 84   |
| PR05 | 85   | 86   | 87   | 88   | 89   | 90   | 91   | 92   | 93   | 94   | 95   | 96   | 97   | 98   | 99   | 100  | 101  | 102  | 103  | 104  | 105  |
| PR06 | 106  | 107  | 108  | 109  | 110  | 111  | 112  | 113  | 114  | 115  | 116  | 117  | 118  | 119  | 120  | 121  | 122  | 123  | 124  | 125  | 126  |
| PR07 | 127  | 128  | 129  | 130  | 131  | 132  | 133  | 134  | 135  | 136  | 137  | 138  | 139  | 140  | 141  | 142  | 143  | 144  | 145  | 146  | 147  |
| PR08 | 148  | 149  | 150  | 151  | 152  | 153  | 154  | 155  | 156  | 157  | 158  | 159  | 160  | 161  | 162  | 163  | 164  | 165  | 166  | 167  | 168  |
| PR09 | 169  | 170  | 171  | 172  | 173  | 174  | 175  | 176  | 177  | 178  | 179  | 180  | 181  | 182  | 183  | 184  | 185  | 186  | 187  | 188  | 189  |
| PR10 | 190  | 191  | 192  | 193  | 194  | 195  | 196  | 197  | 198  | 199  | 200  | 201  | 202  | 203  | 204  | 205  | 206  | 207  | 208  | 209  | 210  |
| PR11 | 211  | 212  | 213  | 214  | 215  | 216  | 217  | 218  | 219  | 220  | 221  | 222  | 223  | 224  | 225  | 226  | 227  | 228  | 229  | 230  | 231  |
| PR12 | 232  | 233  | 234  | 235  | 236  | 237  | 238  | 239  | 240  | 241  | 242  | 243  | 244  | 245  | 246  | 247  | 248  | 249  | 250  | 251  | 252  |
| PR13 | 253  | 254  | 255  | 256  | 257  | 258  | 259  | 260  | 261  | 262  | 263  | 264  | 265  | 266  | 267  | 268  | 269  | 270  | 271  | 272  | 273  |
| PR14 | 274  | 275  | 276  | 277  | 278  | 279  | 280  | 281  | 282  | 283  | 284  | 285  | 286  | 287  | 288  | 289  | 290  | 291  | 292  | 293  | 294  |
| PR15 | 295  | 296  | 297  | 298  | 299  | 300  | 301  | 302  | 303  | 304  | 305  | 306  | 307  | 308  | 309  | 310  | 311  | 312  | 313  | 314  | 315  |
| PR16 | 316  | 317  | 318  | 319  | 320  | 321  | 322  | 323  | 324  | 325  | 326  | 327  | 328  | 329  | 330  | 331  | 332  | 333  | 334  | 335  | 336  |
| PR17 | 337  | 338  | 339  | 340  | 341  | 342  | 343  | 344  | 345  | 346  | 347  | 348  | 349  | 350  | 351  | 352  | 353  | 354  | 355  | 356  | 357  |
| PR18 | 358  | 359  | 360  | 361  | 362  | 363  | 364  | 365  | 366  | 367  | 368  | 369  | 370  | 371  | 372  | 373  | 374  | 375  | 376  | 377  | 378  |
| PR19 | 379  | 380  | 381  | 382  | 383  | 384  | 385  | 386  | 387  | 388  | 389  | 390  | 391  | 392  | 393  | 394  | 395  | 396  | 397  | 398  | 399  |
| PR20 | 400  | 401  | 402  | 403  | 404  | 405  | 406  | 407  | 408  | 409  | 410  | 411  | 412  | 413  | 414  | 415  | 416  | 417  | Blank | Blank | Blank |

FIG. 3

METHOD FOR ISOLATING DNA MOLECULES BY GENERATING A PROGENITOR COLLECTION CATALOG

BACKGROUND

The subject matter described herein relates to systems and methods for isolating DNA molecules, specifically, an arrayed collection of DNA molecules.

Over the last decade, next-generation sequencing has dramatically improved the accessibility of genetic information. However, the percentage of genes of unknown function in a genome sequence remains approximately the same, about 30-40%, as it did a decade ago. This situation is more acute for more esoteric microbes that offer unique genetic resources to genetic engineering and synthetic biology.

Genetic screening of arrayed collections of clonal isolates remains a common method of characterization for many non-fitness-related microbial phenotypes including drug targets, virulence factors, and secondary and cryptic metabolism. Genetic screens conducted with whole genome knock-out collections such as the Yeast Knockout Collection (YKO)10 and the Keio Collection of $E.$ $coli$ gene deletion mutants are widely used for gene function discovery. Typically, construction of these collections requires large investments in time, cost and technical expertise. As a result, only a small number of their type have been built to date. This has motivated the development of methods that use next-generation sequencing and combinatorial pooling to reduce the cost and increase the ease of annotation of arrayed collections of mutants created by random transposon mutagenesis. These breakthroughs have facilitated the construction of a number of condensed curated gene knockout collections of pathogenic organisms and surrogates.

Despite the considerable cost- and labor-saving advantages of recent combinatorial pooling methods, their reliance upon liquid-handling robotics can be an obstacle to widespread adoption. This barrier has spurred ongoing development of rapid, easy to use, and low cost methods for combinatorial pooling.

SUMMARY OF THE DISCLOSED TECHNOLOGY

The disclosed technology relates to systems and methods for isolating DNA molecules, specifically, an arrayed collection of DNA molecules. The disclosed technology uses a set of algorithms that compensate for the low complexity of combinatorial pools produced by manual methods. The disclosed technology, also, allows for annotation of extremely large random transposon mutant collections thereby ensuring high coverage of complicated microbial genomes.

In one implementation, a method for isolating a collection of DNA can comprise the steps of: providing a transposon mutant collection, the transposon mutant collection being stored in a plurality of wells; dispatching aliquots from each well in the transposon mutant collection to a set of pools in a combinatorial pooling array that uses pool address coordinates, the aliquots being dispatched to the set of pools based on a location of the aliquots within the transposon mutant collection; constructing an amplicon library, the amplicon library including a sequencing dataset; parsing the sequencing dataset to a set of putative transposon insertion locations and pool address coordinates; calculating a likelihood for each location and pool address coordinates within the set of putative transposon insertion locations and pool address coordinates using a Bayesian inference algorithm informed by internal self-consistency; generating a progenitor collection catalog based on location and pool address coordinates verified in the calculating step.

In some implementations, the method can further comprise the steps of sequencing a random set of mutants from the progenitor collection catalog; and verifying the progenitor collection catalog when sequencing data from the sequencing step corresponds to the progenitor collection catalog.

In some implementations, the pool address coordinates can relate to plates being arranged in a grid. In some implementations, the grid can be a four-dimensional grid.

In some implementations, the amplicon library can be constructed using a semi-random nested PCR reaction that amplifies a transposon insertion site for every mutant in each pool and adds sequencer compatible flow-cell binding sequences and barcodes thereby allowing the pools to be combined and sequenced in parallel.

In some implementations, the parsing step can further comprise the steps of: (i) constructing a pool presence table; and (ii) deducing locations of mutants using the pool presence table.

In some implementations, the progenitor collection catalog can be used to direct a construction of a non-redundant quality-controlled whole-genome knockout collection.

In some implementations, mutants of the progenitor collection catalog in singly-occupied wells can be re-arrayed into a first portion of condensed collection plates. In some implementations, mutants of the progenitor collection catalog that co-occupy a well can be colony purified.

In some implementations, the method can further comprise the step of predicting, using an algorithm, how many colonies must be picked in order to isolate a mutant of interest in each co-occupied well. In some implementations, the method can further comprise the steps of picking and adding the colonies to the condensed collection plates.

In some implementations, the method can further comprise the steps of re-pooling the condensed collection plates; and validating the condensed collection plates with a second round of sequencing. The second round of sequencing can use orthogonal sequence analysis. The orthogonal sequence analysis can validate a sequence content of all wells in the quality-controlled collection by calculating the intersection of the 4 transposon coordinate sets that correspond to the 4 pool coordinates of the well. In some implementations, if the intersection of the 4 transposon coordinate sets that correspond to the 4 pool coordinates of the well contained one of the predicted genomic coordinates for that well, the location is marked as correct. In some implementations, if the intersection contained a coordinate isolated by colony purification, the coordinate was marked as containing a desired mutant.

In some implementations, one representative of each type of mutant in a colony purified set is selected for insertion into a quality-controlled collection.

BRIEF DESCRIPTION OF THE DRAWINGS

FIG. 1$b$ is a representation of a combinatorial pooling array used with the disclosed technology;

FIG. 1$c$ is a workflow for amplicon generation, sequencing and location inference used with the disclosed technology;

FIG. 3 is a representation of a combinatorial pooling array used with the disclosed technology;

DETAILED DESCRIPTION

The disclosed technology is generally directed systems and methods for isolating DNA molecules, specifically, an arrayed collection of DNA molecules. In one implementation, the disclosed technology relates to a method for the construction of whole-genome knockout collections for a wide range of microorganisms. The method can use 4-dimensional combinatorial pooling, next-generation sequencing and specially programmed processors running unique algorithms to rapidly process and then accurately annotate an extremely large progenitor transposon insertion mutant collection. This method achieves saturating coverage of complex microbial genomes within the collection.

In certain embodiments, the generation, combinatorial pooling and annotation of these highly oversampled progenitor collections and their subsequent algorithmically guided condensation and curation into high-quality collections suitable for rapid genetic screening and gene discovery are presented. For further description, see Michael Baym et al, *Rapid construction of a whole-genome transposon insertion collection for Shewanella oneidenis by Knockout Sudoku*, Nature Communications, (2016); and see Isao Anzai et al., *Knockout Sudoku, a Method for Rapidly Curating Gene Disruption Collections*, Peer Preprints, (2016), both of which are hereby incorporated by reference in their entireties.

In one implementation, the disclosed technology can construct a curated, condensed, non-redundant whole-genome knockout collection by annotation of a highly oversampled progenitor transposon insertion mutant collection and condensation by choosing a single representative disruption mutant for each non-essential gene. A 4-dimensional combinatorial pooling array can be used to prepare a library for a next generation sequencing experiment. The sequencing dataset can be deconvolved using unique algorithms to identify and locate mutants thereby generating a quality controlled collection.

Figure 1A:
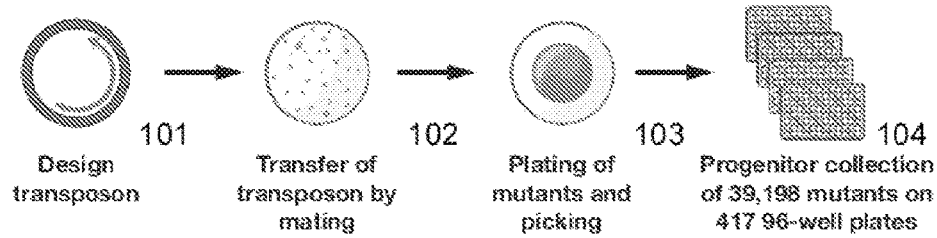
FIG. 1$a$ is a workflow for generation of a transposon insertion mutant collection used with the disclosed technology.

As shown in FIG. 1a, a transposon insertion mutant collection can be generated by designing a transposon (Step 101), transferring the transposon by mating (Step 102), plating and picking the mutants (Step 103) and forming the progenitor collection (Step 104).

The plating method can be implemented using a combinatorial pooling array shown in FIG. 1b as will be described more fully below. This combinatorial pooling array can be pooled with a 96-channel pipettor and allows a research team to pool a single 96-well plate in approximately one minute, compared with almost 2 hours in a robotic scheme. Please note, other size pipettors can be used, e.g., an n-channel pipettor wherein n>1. In practice, a small team can pool and cryopreserve a 40,000 member progenitor collection in just a single day, which is sufficient to achieve high coverage of a microbial genome with approximately 3,500-4,000 nonessential genes. In certain embodiments, the plating method can achieve plating of a 100 million member progenitor collection or more by speeding up colony picking protocols, using a larger pipettor, using variations of other conventional techniques, automation, robotics and combinations thereof.

Using the progenitor collection formed in Step 104, an amplicon library can be constructed (Step 110). The construction of the amplicon library can utilize a semi-random nested PCR reaction that amplifies a transposon insertion site for every mutant in each pool. This semi-random nested PCR reaction can add sequencer compatible flow-cell binding sequences and barcodes to the amplicon library which allows the pools to be combined and sequenced in parallel (Step 111). The presence of amplicons within the sequencing dataset can permit mutants to be located.

As the progenitor collection size grows, the number of transposon mutants that appear at multiple locations can rise in tandem. The appearance of identical mutants in multiple wells, along with cross-contamination at the pooling step, can complicate mutant location by producing a large number of artifactual assignments relative to the number of real locations. To compensate for the above, the likelihood of each of these location assignments can be calculated by a Bayesian inference algorithm informed by internal self-consistency within the sequencing dataset, allowing a user to disregard artifacts and find a real location of these mutants (Step 112).

The large size of the progenitor collections that can be analyzed by the disclosed technology affords a wide choice of transposons insertion positions for each gene. Additionally, an assessment of cross-contamination can allow a user to focus their efforts on mutant isolation through colony purification and re-arraying of non-redundant set of mutants (Step 113). These steps can reduce the construction time and increase the quality of a quality-controlled collection (Step 114).

Figure 2:
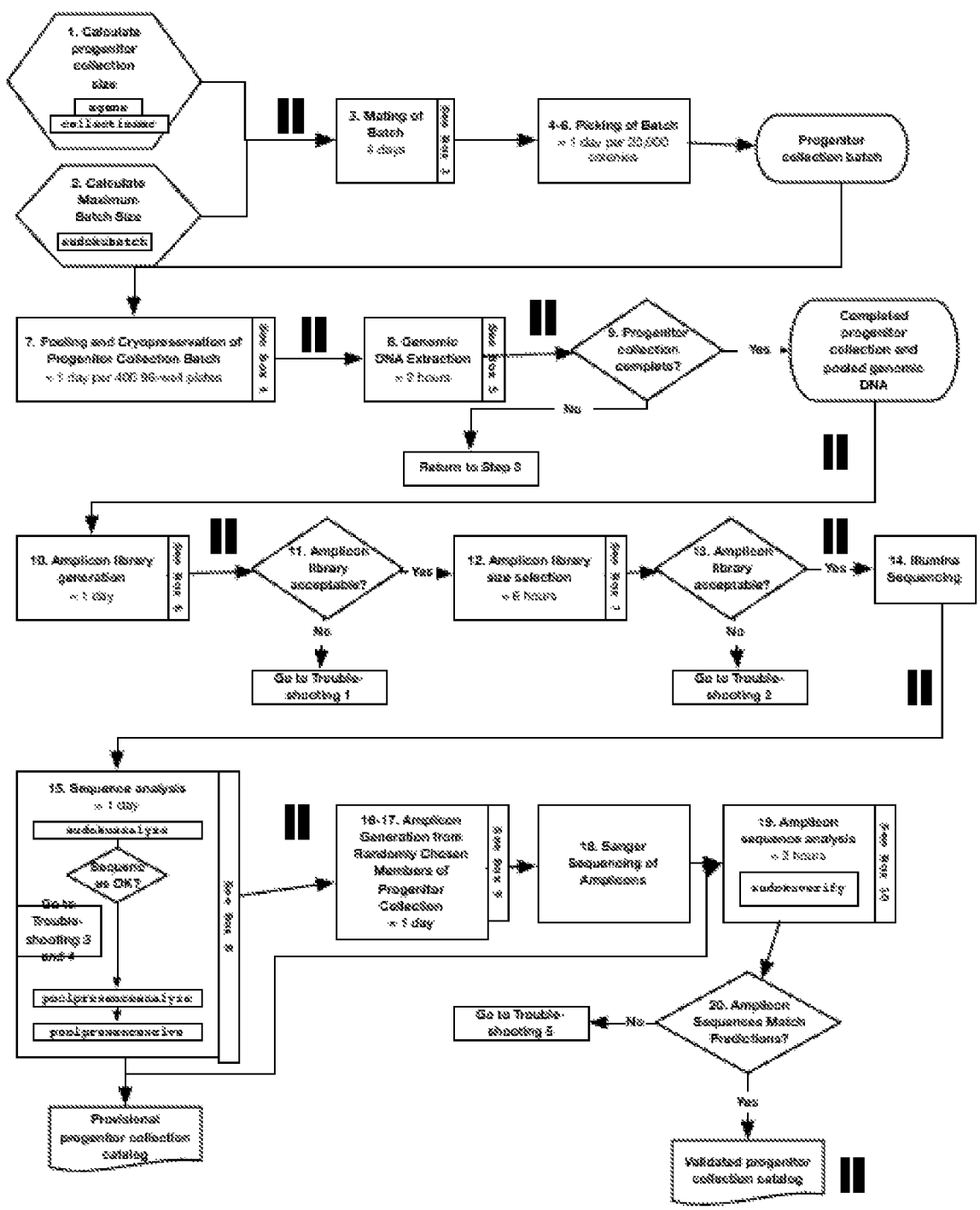
FIG. 2 is a workflow for creation and annotation of a progenitor collection used with the disclosed technology.

FIG. 2 show steps (Steps 1-20) for creating and annotating a progenitor collection. Prior to picking a progenitor collection, to ensure saturating coverage of a genome of a parental organism, a minimum progenitor collection size can be calculated. The calculation can be performed using different models to aid in estimation of the minimum progenitor collection size, $N_p$. In certain embodiments, two models are used; the first model can be an analytical Poisson-based model, which is a function of a number of non-essential genes and provides a baseline minimum for complete coverage of the genome; and the second model can be a Monte Carlo numerical simulation of transposon insertion that takes into account gene location and essentiality data estimates.

In practice, the maximum batch size can be equal to a smallest of: the maximum batch that can be plated ($N_{plate}$), the maximum batch that can be picked ($N_{pick}$) or the maximum batch that can be pooled ($N_{pool}$). If the minimum progenitor collection size needed to achieve saturating coverage of the genome, $N_p$, exceeds $N_{batch}$, the construction of the progenitor collection can be split into separate batches that can be plated, picked, pooled, and cryopreserved separately. This helps ensure the progenitor collection remains healthy and sample viability is less compromised.

Figure 5:
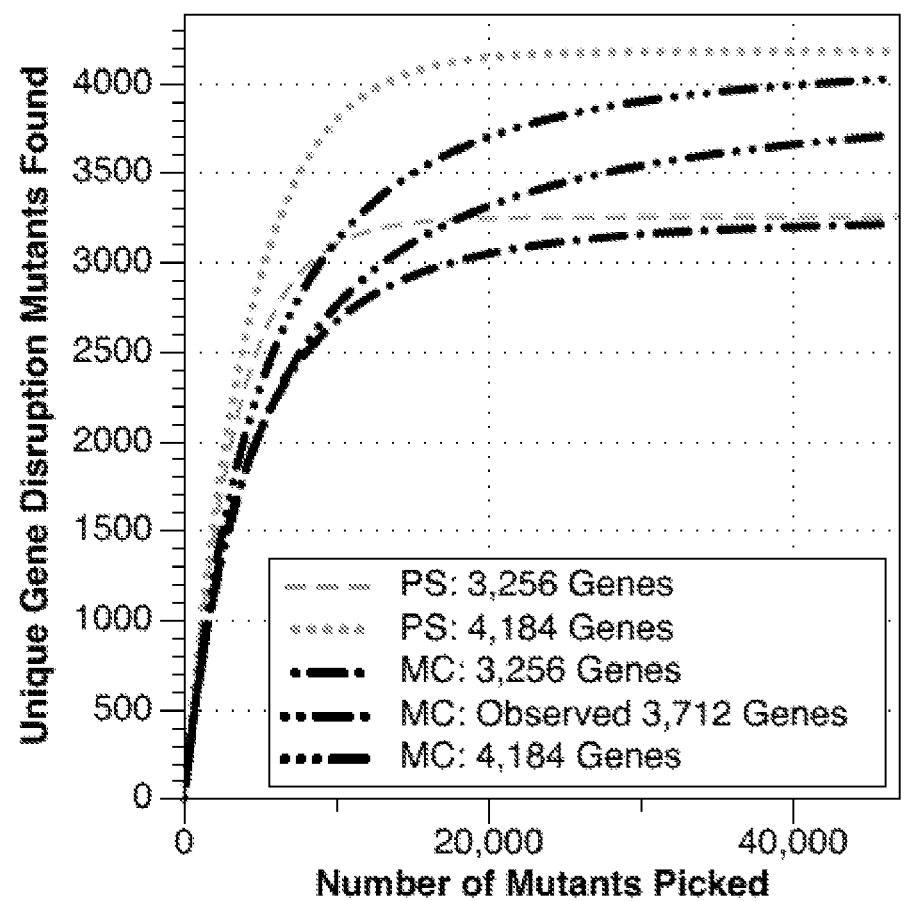
FIG. 5 is a graphical representation of gene counts used with the disclosed technology.

In one implementation, a gene-indexing program can be run to generate an index of all possible transposon insertion locations in a parental organism genome and its associated locus. The output of the gene-indexing program can be prepared as a collection input file for a collection program. The collection input file can be run within the collection program to generate a rarefaction curve. As shown in FIG. 5, the rarefaction curve estimates genome coverage as a function of progenitor collection size. (Step 1).

In Step 2, progenitor collection construction parameters can be calculated using a batch size program to calculate the maximum size of a batch of transposon mutants that can be pooled without compromising sample viability. That is, $N_{batch}$ can be calculated along with picking a sub batch size, the picking time per day, total days of picking and acceptable rest time between picking and pooling.

In Step 3, a mating mixture can be constructed by plating out a pickable and poolable batch of colonies, as calculated in step 2. In this step, the disclosed technology determines the transposon insertion mutant density by plating a dilution series and then repeats this step for a second time to generate the progenitor collection. The density of transposon insertion mutants in the mating mixture can be calculated by counting colonies on the dilution series.

The colonies can be robotically picked into 96-well plates containing a growth media with antibiotics. (Step 4). In some implementations, each plate can be sealed with a sterile Aeraseal membrane. In one implementation, timing estimates can be based on the use of a Norgren Systems CP7200 colony picking robot adjusted to accommodate the sensitivities of an organism such as S. oneidensis.

In Step 5, mutant colonies can be grown. For example, a mutant colony of S. oneidensis can be grown in a shaking incubator at ~900 rpm at preferred growth temperature of ~30° C. for ΔT saturation of ~21 hours. (Please note that if the number of picking days calculated in step 2 is greater than 1, return to step 4 until the colony batch is complete. (Step 6).)

In Step 7, the progenitor collection batch can be pooled. Furthermore, this process is highly amenable to parallelization if more than one 96-channel pipettor is available.

Figure 1B:
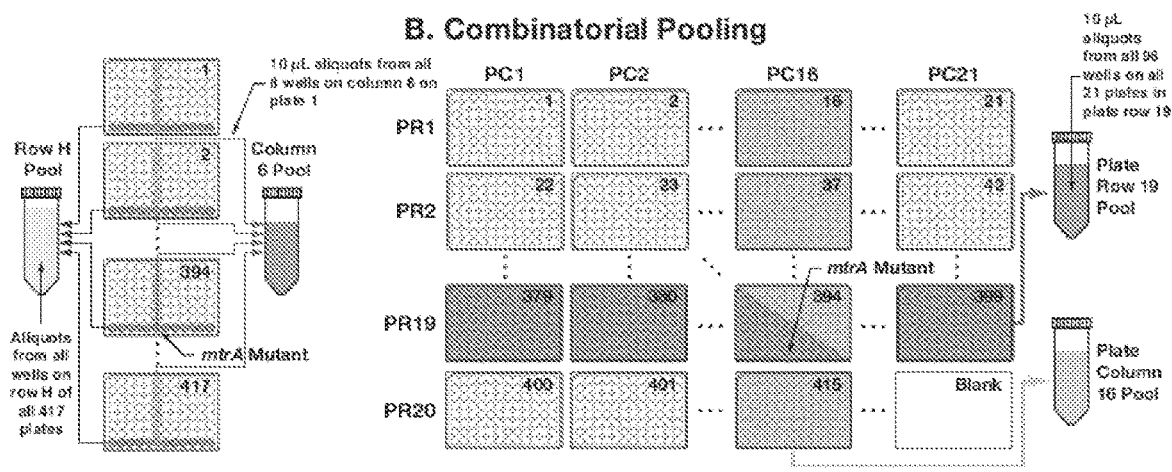
Figure 1C:
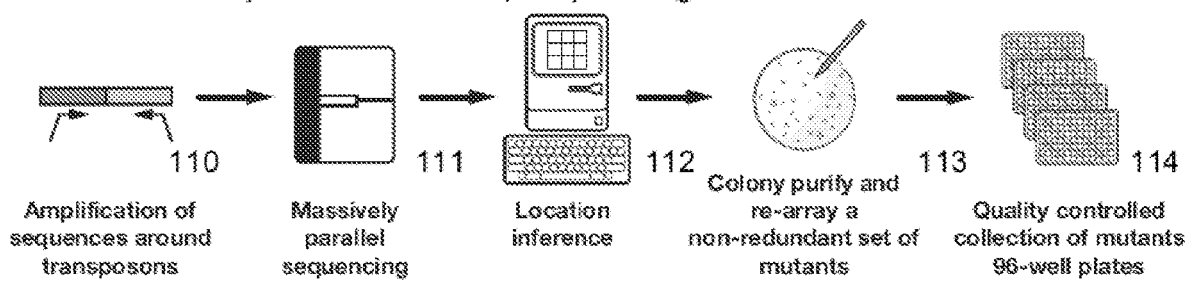

The disclosed technology can use a four-dimensional combinatorial pooling array that can be easily performed with multi-channel pipettors (e.g., n-channel pipettor where n>1) while minimizing sample preparation costs (FIG. 1b). In one example, shown in FIG. 3, 417 plates can be used to pool a progenitor collection of 39,918 mutants. Each plate can be assigned a position within a virtual 20×21 grid, giving each plate two coordinates: a plate-row (PR) and a plate-column (PC). The assignment of 2 coordinates per plate allows the cost of sequencing library construction to grow only with the square root of the number of plates. Aliquots of culture from each well in the collection can be dispatched to four pools that uniquely corresponded to the address of the well within the plate grid and the individual plate. For example, in FIG. 1b, a mutant with a disruption in the mtrA cytochrome that was located in well H6 on plate 394 can be dispatched to the Row H, Column 6, PR 19, and PC 16 pools. In total, 61 address pools (20 plate-row×21 plate-column pools, 8 row×12 column pools) can be filled. The entire progenitor collection can be pooled and cryopreserved in a single day using a 96-channel pipettor. The address pools can be used to generate 61 barcoded amplicon libraries that encode the genomic locations of the transposons present within each pool.

In Step 8, genomic DNA can be extracted from the pools. This procedure can use a Zymo Research genomic DNA mini-prep kit for extraction but other kits are contemplated. In Step 9, a research team can analyze the plates to ensure saturating coverage of the genome. (If more batches of colonies are needed to achieve saturating coverage of the genome, return to step 3. Otherwise, continue to step 10.)

In Step 10, pool amplicon libraries can be generated from the pooled progenitor collection mutants. Pool amplicon library construction for the disclosed technology can be generated using a 2-step nested PCR reaction. This reaction amplifies a portion of the chromosome adjacent to the transposon present in each collection member and adds Illumina TruSeq flow-cell-binding and read-primer-binding sequences to the 3' and 5' ends of the amplicon while replacing the standard Illumina index sequence with a custom barcode sequence for each pool.

Figures 4A, 4B:
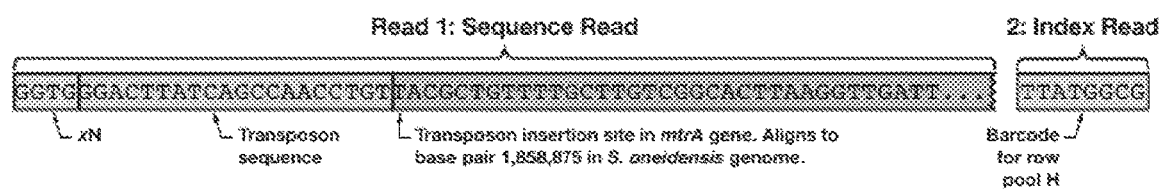
FIG. 4a is a representation of a read compilation used with the disclosed technology.
FIG. 4b is a representation of a pool presence table compilation used with the disclosed technology.

Molecular weight distributions of the pool amplicon libraries can be inspected using diagnostic gels. (Step 11). The pool amplicon libraries can be collected into a single vial and purified by molecular weight. The purification step can produce a sequencing library with a molecular weight distribution suitable for sequencing on an Illumina device. (Step 12). The pool amplicon libraries can be sequence by Illumina Sequencing. (Step 13). In Step 14, the combined libraries can be sequenced, e.g., on 2 lanes of an Illumina HiSeq in 67 bp single-end read mode, (for example, see FIG. 4a, which shows the sequence GGTGGGACTTATCAGC-CAACCTGTTACGCTGTTTTGCTTGTCGGCACT-TAAGGTTGAT TTTATGGCG (SEQ. ID NO: 1)).

Figure 8:
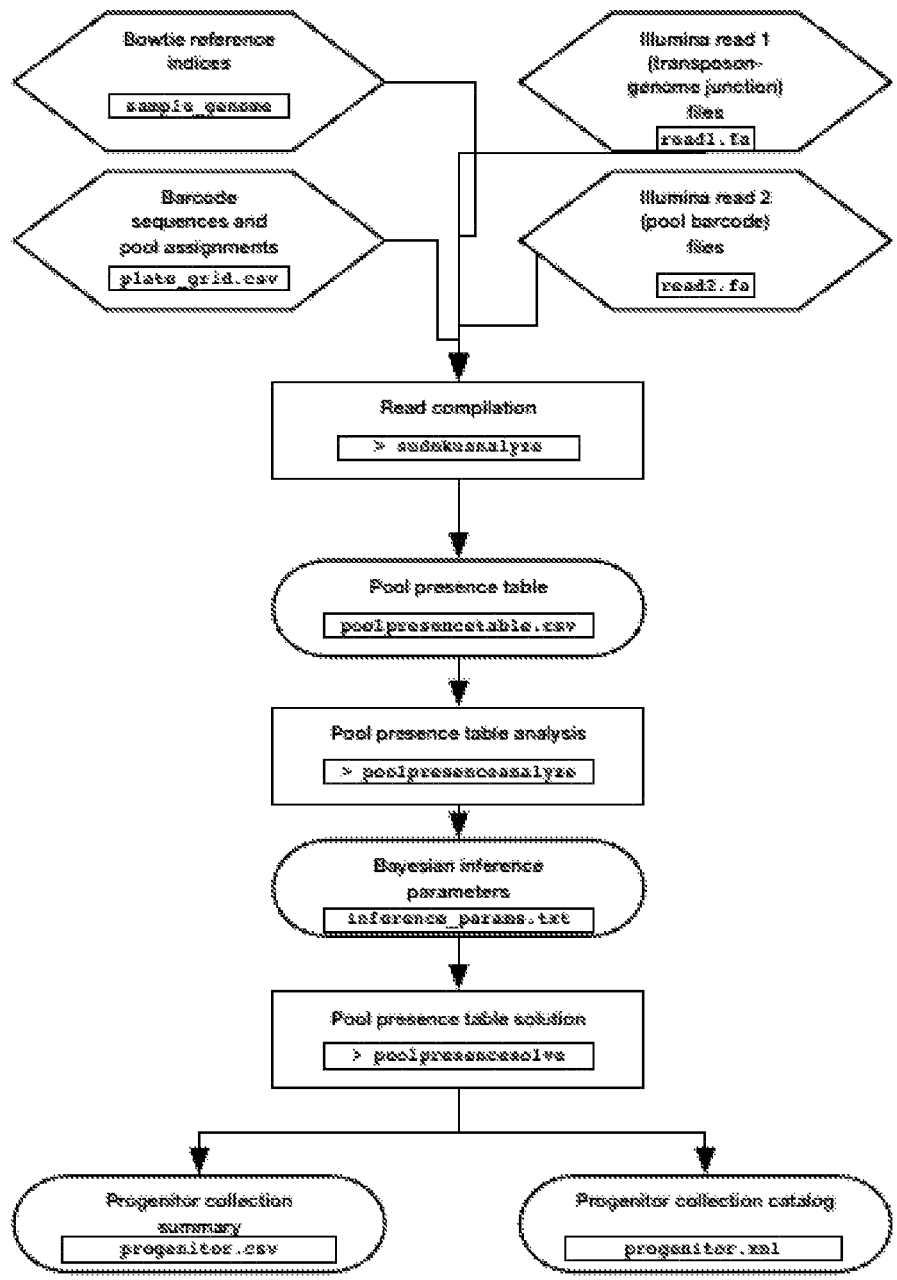
FIG. 8 is a software workflow for a progenitor collection catalog solution used with the disclosed technology.

In Step 15, the progenitor collection contents can be solved using a data analysis procedure that predicts the contents of each well in the progenitor collection. In FIG. 8, a workflow for the solution of the progenitor collection is shown. A combined input file can contain (1) a BOWTIE2 index 200 built for genomes of interest, (2) a barcode file 201 that contains a list of barcode sequences and the corresponding pool assignments, (3) transposon junction files 202 from the Illumina read and (4) pool barcode files 203 from the Illumina read is prepared. A sequencing dataset analysis program 204 analyzes the combined input file to generate a pool presence table 205, e.g., see FIG. 4b. In other words, for each genomic location, the number of reads with a given barcode are counted to construct the pool presence table. The pool presence table 205 can be examined to find a percentage of reads that contain a valid pool barcode and transposon sequence that can be aligned to a reference genome. The examination results in an analysis input file for a pool presence table analysis program 206.

The pool presence table analysis program 206 is run to determine the effect of read count threshold on the taxonomy of a pool presence table solution. The output of the pool presence table analysis program 206 is used to decide upon a read count threshold, e.g., a read count threshold of 5 reads (this should only be decided after careful examination of the output of pool presence table analysis program, a read count threshold that maximizes the number of transposon locations that unambiguously map to locations within the progenitor collection is desired).

The read count threshold can be used to prepare a threshold input file for a pool presence table read count ratio fitting program. The pool presence table read count ratio fitting program, by deduction, can generate a set of putative transposon insertion locations and pool address coordinates. Bayesian inference parameters can also be calculated for input into a pool presence table solver program 208. The pool presence table solver program 208 is run using the set of putative transposon insertion locations and pool address coordinates to obtain predictions for a progenitor collection summary 209 and a progenitor collection catalog 210.

In Step 16, the predictions of the progenitor collection summary 209 and the progenitor collection catalog 210 can be tested by picking a random set of 10 to 94 mutants from the progenitor collection and re-arraying them into a single 96-well plate. These mutants can be grown to saturation. Amplicons from each mutant can be generated using a sanger verification program (Step 17). For example, the amplicons can be sent for standard Sanger sequencing with PCR product clean up. (Step 18). (Sanger sequencing is a technique for DNA sequencing based upon the selective incorporation of chain-terminating dideoxynucleotides (ddNTPs) by DNA polymerase during in vitro DNA replication.) The predictions of the progenitor collection summary 209 and the progenitor collection catalog 210 can be tested against the results of Sanger sequencing. That is, a verification input file for a prediction verification program is prepared along with a description of the sequencing results. The prediction verification program is run. (Step 19). If the predictions match the results of Sanger sequencing (Step 20), the predictions are verified and the workflow continues to Step 21-38 of FIG. 6.

The progenitor collection catalog can be used to direct the construction of a non-redundant, quality-controlled, whole-genome knockout collection. In use, a single representative mutant can be selected for each gene disrupted in the progenitor collection by an algorithm that balances the likelihood that the mutant will knock out the function of a gene with the ease of isolation from any well co-occupants. These selected mutants can go through a purification triage where those in singly-occupied wells (i.e., a well that contains a single mutant species) are re-arrayed. Desirable mutants that co-occupy a well can still be isolated. For each co-occupied well, the algorithms of the disclosed technology can predict the smallest number of colonies that must be picked to isolate a mutant of interest. These colonies are picked and then added to condensed collection plates. The entire condensed collection can be re-pooled and validated by a second round of sequencing and alternative, orthogonal sequence analysis. One representative of each type of mutant in the colony purified set is selected for insertion into the quality-controlled collection; further, mutants for any genes still lacking representatives are also added.

Figure 6:
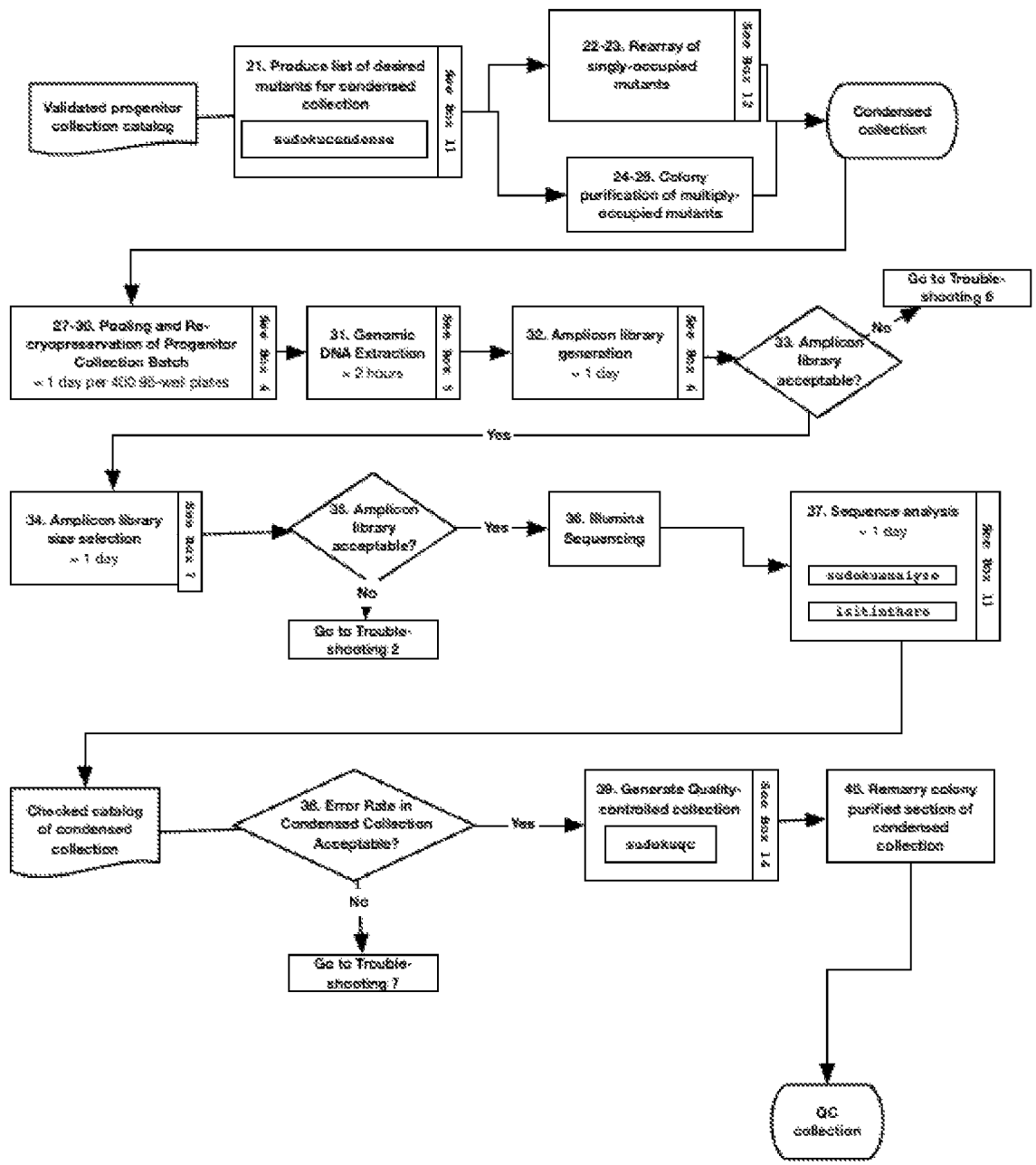
FIG. 6 is a workflow for creation of condensed and quality-controlled collections used with the disclosed technology.

FIG. 6 shows the steps (Steps 21-40) for creating a condensed and quality-controlled collection. In Step 21, mutants from the progenitor collection are selected for a condensed collection using a progenitor collection condensation program. The progenitor collection condensation program is used to select a complete, non-redundant set of gene disruption mutants from the progenitor collection and generate instructions to retrieve and re-array them. In use, an condense input file for the progenitor collection condensation program is prepared and executed by the progenitor collection condensation program to obtain condensed collection instructions and to select single-occupancy wells and multiple-occupancy wells for the condensed and quality-controlled collection.

The condensed progenitor collection can be prepared by re-arraying the selected single-occupancy wells in the progenitor collection into a first section of the condensed collection using the condensed collection instructions generated in step 21. (Steps 22-23). The re-array and colony purification instructions produced by the collection condensation program can be converted to generate re-array instructions for a colony picking robot. In Steps 24-26, simultaneous to Steps 22-23, the selected multiple-occupancy wells can be colony purified into a second section of the condensed collection using the condensed collection instructions generated in step 21.

In Steps 27-30, re-arrayed plates can be frozen at −80° C. with cryoprotectant. The identities of mutants in the condensed collection can be validated by re-pooling and re-sequencing. The re-pooling and re-sequencing can be arranged in an approximately square plate grid. A suggested grid can be included in the condensed collection instructions from step 21. The condensed collection can be retrieved from the freezer, if necessary, pooled, and frozen or re-frozen.

Genomic DNA can be extracted from the condensed collection (Step 31) and pool amplicon libraries for the condensed collection can be generated (Step 32). The pool amplicon libraries for the condensed collection can be inspected using gel electrophoresis. (Step 33). The pool amplicon libraries can be collected into single vial and purified by molecular weight. (Step 34). The purified amplicon libraries can be submitted for quality control by an Illumina sequencing service. (Step 35). In Step 36, the purified amplicon libraries can be sequenced on 1 lane of an Illumina HiSeq 2500 in single end 67 bp read mode.

Figure 7:
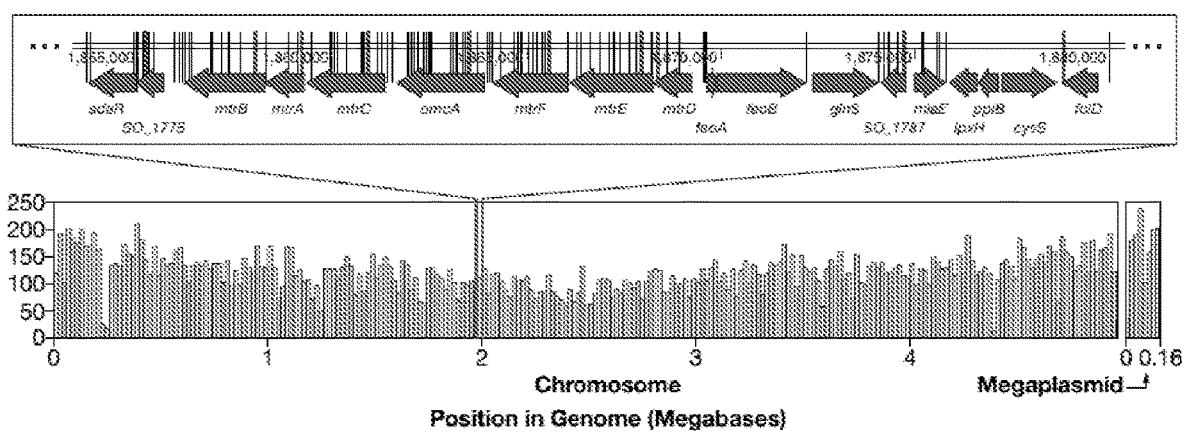
FIG. 7 is a representation of densities and locations of transposons in a progenitor collection used with the disclosed technology.

In Step 37, the identities of the mutants in the condensed collection can be validated by an orthogonal data analysis program. The orthogonal data analysis program contains an algorithm for testing the presence of a particular sequence in a particular well. This is useful for selection and condensation of the colony purified section of the condensed collection. The orthogonal data analysis program is run using an orthogonal input file prepared from the reads of the Illumina sequencing. (For examples of transposon density and locations, see FIG. 7). In one implementation, the orthogonal sequence analysis can determine sequence content for all the wells in the quality-controlled collection by calculating the intersection of the 4 transposon coordinate sets that correspond to the four pool coordinates of the well. If the intersection of the 4 transposon coordinate sets that correspond to the four pool coordinates of the well contained one of the predicted genomic coordinates for that well, the location is marked as correct. If the intersection contained a coordinate isolated by colony purification, the coordinate can be marked as containing a desired mutant.

In Step 38, the error rate of the condensed collection is checked. A 4-8% error rate is acceptable.

In Step 39, a quality-controlled collection is generated using a quality control program. The quality control program can generate instructions for further condensation of the colony purified second section of the condensed collection and addition of any missing mutants. This quality control program takes as input the output of the orthogonal data analysis program and outputs instructions for re-arraying wells in the colony purified section of the condensed collection to select only a single correct representative. Additionally, the quality control program can provide a list of genes missing from the condensed collection and can give instructions for their retrieval from the progenitor collection. In Step 40, the re-array instructions can be utilized to generate a condensed and quality-controlled collection.

Figure 9:
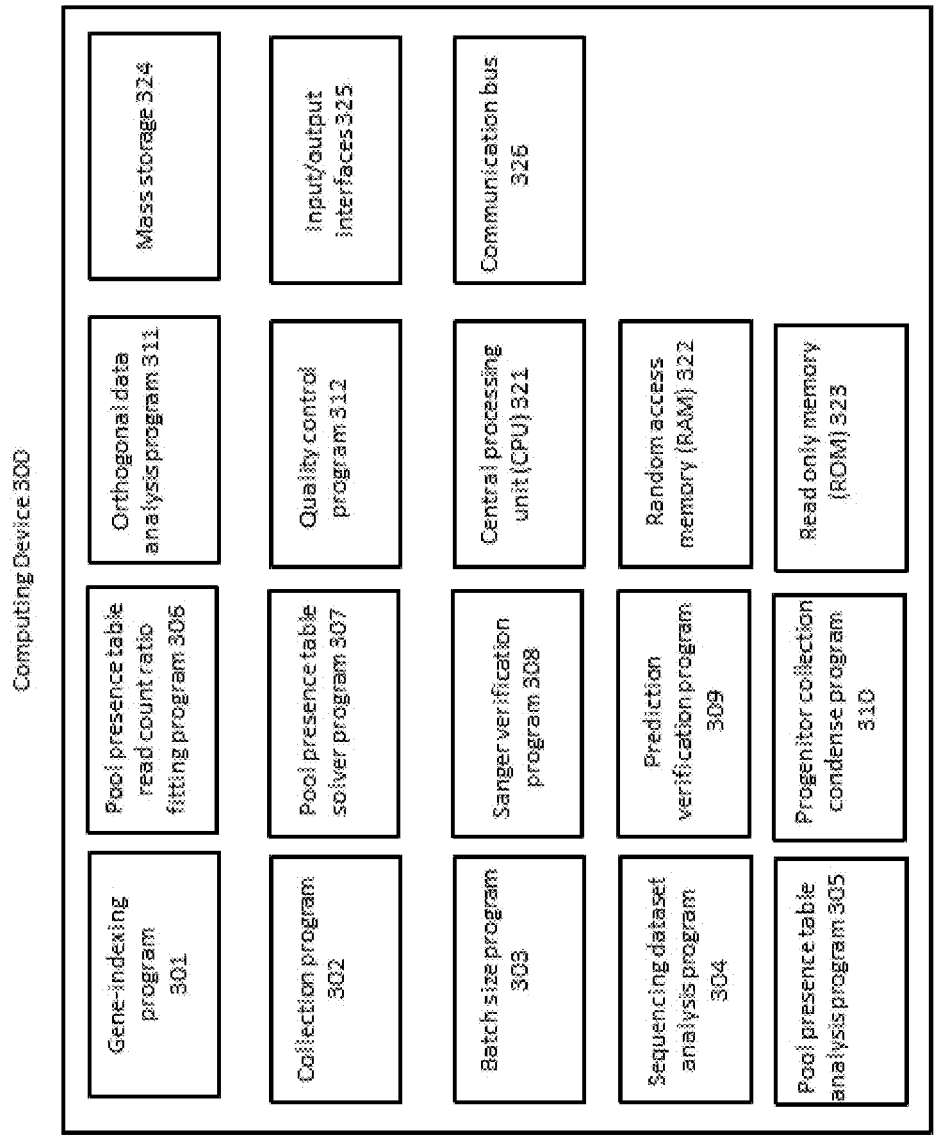
FIG. 9 block diagram of a computing device used with the disclosed technology.

The programs associated with the disclosed technology, e.g., the gene-indexing program 301, the collection program 302, the batch size program 303, the sequencing dataset analysis program 304, the pool presence table analysis program 305, the pool presence table read count ratio fitting program 306, the pool presence table solver program 307, the sanger verification program 308, the prediction verification program 309, the progenitor collection condensation program 310, the orthogonal data analysis program 311 and the quality control program 312, can reside in a computing device 300 as shown in FIG. 9. The computing device 300 may comprise a central processing unit (CPU) 321, random access memory (RAM) 322, read only memory (ROM) 323, mass storage 324 (e.g. hard drive) and input/output interfaces 325 all interconnected by a common communication bus 326. I/O interfaces 326 may comprise a set of different interfaces providing means of communication of the computing device 300 with external devices. For those skilled in the art it is understandable, that this may include many different types of wired or wireless interfaces including, but not limited to: USB, Firewire, RS232, parallel port, HDMI, DVI, VGA monitor port, Bluetooth. The I/O interfaces 326 may also include networking interfaces including, but not limited to: WiFi (e.g. IEEE 802.11) or Ethernet. The foregoing types of interfaces are given as an example only, as any means of one or bi-directional communication with external devices are within a scope of the invention. The external devices connected to the computing device 3000 through I/O interfaces 3296 may comprise a screen, keyboard, mouse, printer, camera, microphone or a handheld device 200. One skilled in the art understands that the above list is only exemplary. One skilled in the art understands also, that the computing device must not necessarily include all the presented elements. For example, the invention could work also with a computing device 300 not including ROM 323 or mass storage 325. The computing device 300 may be a personal computer, a laptop, a notebook, a desktop computer, a workstation, a server, a tablet, a mobile phone or any other device on which the programs of the disclosed technology can be run.

According to one embodiment of the invention, the programs 301-312 can be implemented as software running on a processor (CPU) 101 being part of a computing device 300. The programs associated with the disclosed technology can be available as a complete software package or individual software components.

The particular naming of the components, capitalization of terms, the attributes, data structures, or any other programming or structural aspect is not mandatory or significant, and the mechanisms that implement various features may have different names, formats, or protocols. Further, the system may be implemented via a combination of hardware and software, as described, or entirely in hardware elements. Also, the particular division of functionality between the various system components described herein is merely for purposes of example, and not mandatory; functions performed by a single system component may instead be performed by multiple components, and functions performed by multiple components may instead performed by a single component.

Some portions of above description present features in terms of algorithms and symbolic representations of operations on information. These algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed embodiments of the disclosure may be implemented using computer programming or engineering techniques including computer software, firmware, hardware or any combination or subset thereof. Any such resulting program, having computer-readable and/or computer-executable instructions, may be embodied or provided within one or more computer-readable media, thereby making a computer program product, i.e., an article of manufacture, according to the discussed embodiments of the disclosure. The computer-readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code may be made and/or used by executing the instructions directly from one medium, by copying the code from one medium to another medium, or by transmitting the code over a network.

The foregoing Detailed Description is to be understood as being in every respect illustrative and exemplary, but not restrictive, and the scope of the disclosed technology disclosed herein is not to be determined from the Detailed Description, but rather from the claims as interpreted according to the full breadth permitted by the patent laws. It is to be understood that the embodiments shown and described herein are only illustrative of the principles of the disclosed technology and that various modifications may be implemented by those skilled in the art without departing from the scope and spirit of the disclosed technology. Those skilled in the art could implement various other feature combinations without departing from the scope and spirit of the disclosed technology. Although the embodiments of the present disclosure have been described with specific examples, it is to be understood that the disclosure is not limited to those specific examples and that various other changes, combinations and modifications will be apparent to one of ordinary skill in the art without departing from the scope and spirit of the disclosed technology which is to be determined with reference to the following claims.

The invention claimed is:

1. A method for isolating DNA molecules comprising the steps of:
providing a transposon mutant collection of mutated genes, the mutated genes comprised within living cells, the transposon mutant collection being stored in a plurality of wells;
dispatching aliquots from each well in the transposon mutant collection to a set of pools in a combinatorial pooling array that uses pool address coordinates, the aliquots being dispatched to the set of pools based on a location of the aliquots within the transposon mutant collection;
constructing an amplicon library, the amplicon library including a sequencing dataset;
parsing the sequencing dataset to a set of putative transposon insertion locations and pool address coordinates;
calculating a likelihood that a correct relationship has been identified for each instance of location with pool address coordinates within the set of putative transposon insertion locations and pool address coordinates using a Bayesian inference algorithm informed by internal self-consistency; and
generating a progenitor collection catalog based on the instances of calculated location with pool address coordinates, the progenitor collection catalog comprising pool address coordinates and corresponding sequences.

2. The method of claim 1 further comprising the steps of:
sequencing a random set of mutants from the progenitor collection; and
verifying the progenitor collection catalog when sequencing data from the sequencing step matches the progenitor collection catalog.

3. The method of claim 1 wherein the pool address coordinates relate to plates being arranged in a grid.

4. The method of claim 1 wherein the amplicon library is constructed using a semi-random nested PCR reaction that amplifies a transposon insertion site for every mutant in each pool and adds sequencer-compatible, flow-cell-binding sequences and a custom barcode sequence for each pool, thereby allowing the pools to be combined and sequenced in parallel.

5. The method of claim 1 wherein the parsing step further comprises the steps of:
constructing a pool presence table by counting the number of instances of each of the putative transposon insertion locations with particular pool address coordinates, the pool presence table being the list of one or more most likely addresses based on the number of such instances counted; and
deducing locations of mutants using the pool presence table based on the frequency of a particular putative transposon insertion location with particular pool address coordinates.

6. The method of claim 1 wherein the progenitor collection catalog is used to direct a construction of a non-redundant, quality-controlled, whole-genome knockout collection.

7. The method of claim 6 wherein mutants of the progenitor collection catalog in singly-occupied wells are re-arrayed into a first portion of condensed collection plates.

8. The method of claim 7 wherein mutants of the progenitor collection catalog that co-occupy a well are colony purified.

9. The method of claim 8 further comprising the steps of:
predicting, using an algorithm, how many colonies must be picked in order to isolate a mutant of interest in each co-occupied well.

10. The method of claim 9 further comprising the steps of:
picking and adding the predicted number of colonies to the condensed collection plates.

11. The method of claim 10 further comprising the steps of:
re-pooling the condensed collection plates and
validating the re-pooled, condensed collection plates with a second round of sequencing.

12. The method of claim 11 wherein the second round of sequencing uses a further analysis step for testing the presence of a particular sequence in a particular well, the further analysis step including determining the sequence content of all wells in the quality-controlled collection by calculating the intersection of 4 transposon coordinate sets that correspond to 4 pool coordinates of the well.

13. The method of claim 12 wherein, if the intersection of the 4 transposon coordinate sets that correspond to the 4 pool coordinates of the well contained one of the predicted genomic coordinates for that well, then the location is marked as correct.

14. The method of claim 13 wherein, if the intersection contained a coordinate isolated by colony purification, then the coordinate was marked as containing a desired mutant.

15. The method of claim 14 wherein one representative of each type of mutant in a colony purified set is selected for insertion into the quality-controlled collection.

* * * * *

SEQUENCE LISTING

<160> NUMBER OF SEQ ID NOS: 1

<210> SEQ ID NO 1
<211> LENGTH: 67
<212> TYPE: DNA
<213> ORGANISM: Shewanella Oneidensis MR-1

```
<400> SEQUENCE: 1
ggtgggactt atcagccaac ctgttacgct gttttgcttg tcggcactta aggttgattt      60
tatggcg                                                               67
```